United States Patent [19]
Morfeld et al.

[11] Patent Number: 4,562,842
[45] Date of Patent: Jan. 7, 1986

[54] BLOOD-LOSS MEASUREMENT APPARATUS

[75] Inventors: Diane E. Morfeld, 7268 Casper Dr., San Diego, Calif. 92119; Henri J. A. Charmasson, San Diego, Calif.

[73] Assignee: Diane E. Morfeld, San Diego, Calif.

[21] Appl. No.: 581,792

[22] Filed: Feb. 21, 1984

[51] Int. Cl.$^4$ .............................................. A61B 5/00
[52] U.S. Cl. .................................... 128/638; 128/771; 604/246; 73/434
[58] Field of Search ..................... 128/771, 766, 638; 604/35, 65, 260, 246; 73/434, 863.21, 863.71, 864.81; 177/25, 15, 31

[56] References Cited

U.S. PATENT DOCUMENTS

| | | | |
|---|---|---|---|
| 4,096,859 | 6/1978 | Agarwal et al. | 604/28 |
| 4,168,700 | 9/1979 | Opelt et al. | 128/630 |
| 4,402,373 | 9/1983 | Contal | 128/771 |
| 4,417,585 | 11/1983 | Frank | 128/771 |
| 4,448,207 | 5/1984 | Parrish | 128/771 |

Primary Examiner—Lee S. Cohen
Assistant Examiner—Steven Falk
Attorney, Agent, or Firm—Charmasson & Holz

[57] ABSTRACT

Apparatus for continuously monitoring the loss of blood suffered by a patient in the course of a surgical operation. The apparatus provides a means for sucking the combination of blood and irrigating solution gathered about the incision, and for sequentially measuring the volumes and densities of small samplings of the solution-and-blood mixture being drawn through the conduit leading from the incision area to the suction device. The apparatus relies on the difference between the respective densities of the blood and of the irrigating solution in order to calculate the exact volume of blood contained in each sampling. The blood loss is continuously accumulated and displayed on a visual read-out, so that a corresponding amount of blood can be transfused to the patient in order to maintain his blood pressure throughout the operation.

The apparatus can be operated in a calibration mode, under which blood, then solution, are measured separately to determine their respective densities which will be used in the quantitative analysis of the mixture.

A scale is also provided to weigh sponges, linen etc. which have absorbed blood or some of the blood-and-solution mixture during the surgery. The corresponding calculated volume of blood which they carry is automatically added to the cumulative figure of lost blood.

12 Claims, 10 Drawing Figures

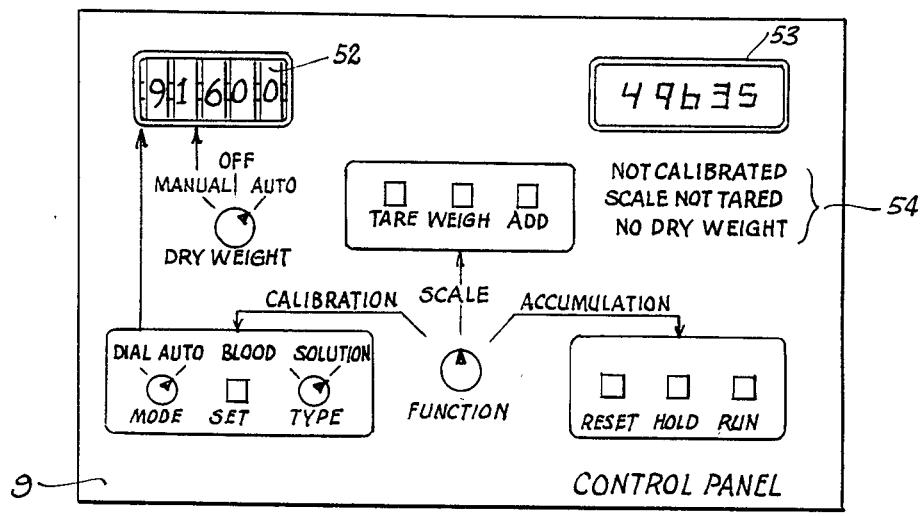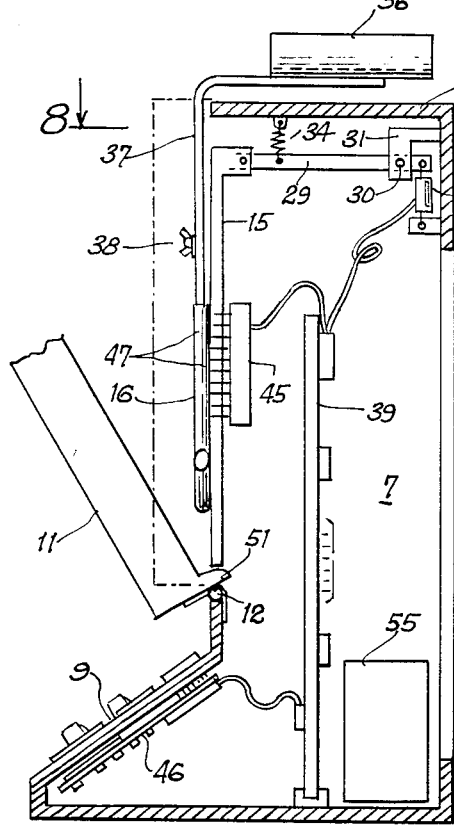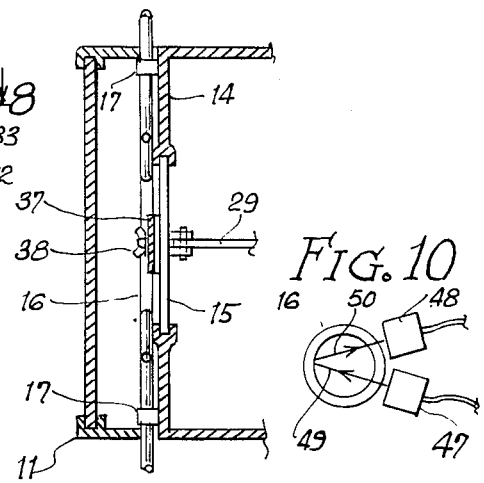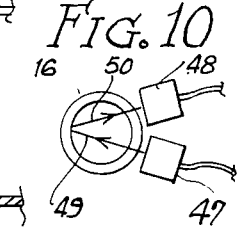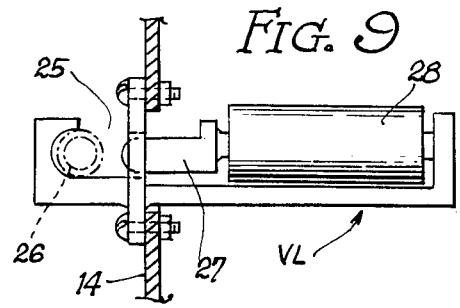

BLOOD-LOSS MEASUREMENT APPARATUS

FIELD OF THE INVENTION

This invention relates to medical apparatus and more particularly to flow measurement devices and other measuring instruments used in connection with transfusion and intravenous infusion apparatus used in operating rooms and intensive care units.

BACKGROUND OF THE INVENTION

In the course of a surgical operation the loss of blood suffered by the patient through the incision must be carefully monitored so that a corresponding volume of blood may be transfused into the patient to avoid loss of blood pressure. For this reason the blood flowing from the incision is carefully gathered by a suction device and accumulated in calibrated containers. The estimation of actual blood loss is complicated by the fact that the area of the incision is continuously irrigated by a cleaning solution which is also drawn by the suction device and ends up mixed up with the blood in the waste containers.

It is, therefore, necessary to also monitor the amount of solution which is being used in the course of the operation. Subtracting the amount of solution used from the volume of mixture gathered in the waste container does not provide an accurate figure of the blood loss due to the fact that a large amount of solution is sprayed around the area of the incision and becomes absorbed by sponges, linen etc.

During a lengthy surgical intervention, the pre-surgical and post-surgical weighing of the solution and mixture can only provide an after-the-fact estimate of the total blood loss, when a continuous or at least periodical estimate would be preferable in order to adjust the amount of transfusion to the actual blood loss and thus avoid sudden, and sometime fatal loss of the patient's blood pressure.

SUMMARY OF THE INVENTION

The principal object of this invention is to provide a means for measuring the volume and density of the irrigating solution and blood mixture which is gathered about an incision during the surgery.

A further object of this invention is to measure from this volume and density and given the respective densities of blood and irrigating solution, the actual volume of blood lost by the patient during the surgery.

It is also an object of this invention to measure this blood loss in a continuous manner throughout the surgery and to accumulate the successive measurements so that the amount of compensating blood transfused into the patient can be carefully adjusted to avoid sudden loss of blood pressure.

Another object of the invention is to provide such an apparatus in which, for sanitary and safety reasons, all the components which come in contact with the patient's blood are disposable and can be quickly removed and replaced at low cost.

This and other valuable objects are achieved by means of an instrument placed in series with the conduit of a suction device designed to draw fluids from around the incision into a waste container. The apparatus causes a small section of the conduit to be intermittently closed; thus trapping small samplings of fluid therein. Each sampling is measured to determine its weight and volume. These measurements are then used to compute the actual density of the sampling. The density is then compared to the respective densities of the mixture components (i.e. blood and irrigating solution) in order to determine the exact amount of blood in each sampling. A cumulative total of blood loss is continuously displayed on the apparatus for use in determining the amount of replacement blood which must be transfused into the patient.

The apparatus further provides means for automatically calibrating the respective densities of the mixture components by manual entry or by actually running a small sample of blood then a small sample of irrigating mixture through the sampling section of the conduit. A scale is also provided to weigh the sponges, linen and other absorbing material which might be used during surgery. The corresponding estimated volume of blood held by these items are automatically added to the cumulative total of blood lost.

BRIEF DESCRIPTION OF THE DRAWING

FIG. 6 is a layout of the control panel;

FIG. 7 is a cross-sectional view taken along line 7—7 of FIG. 2;

FIG. 8 is a partial cross-sectional view taken along line 8—8 of FIG. 2;

FIG. 9 is a side view of a solenoid-controlled clamping valve.

FIG. 10 is a diagram of the optical level sensor.

DESCRIPTION OF THE PREFERRED EMBODIMENT OF THE INVENTION

Figure 1:
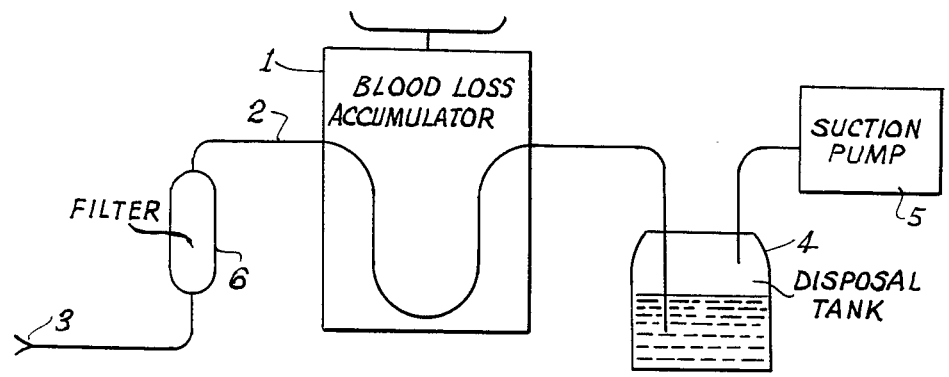
FIG. 1 is a general block diagram illustrating the general operation of the apparatus.
Figure 2:
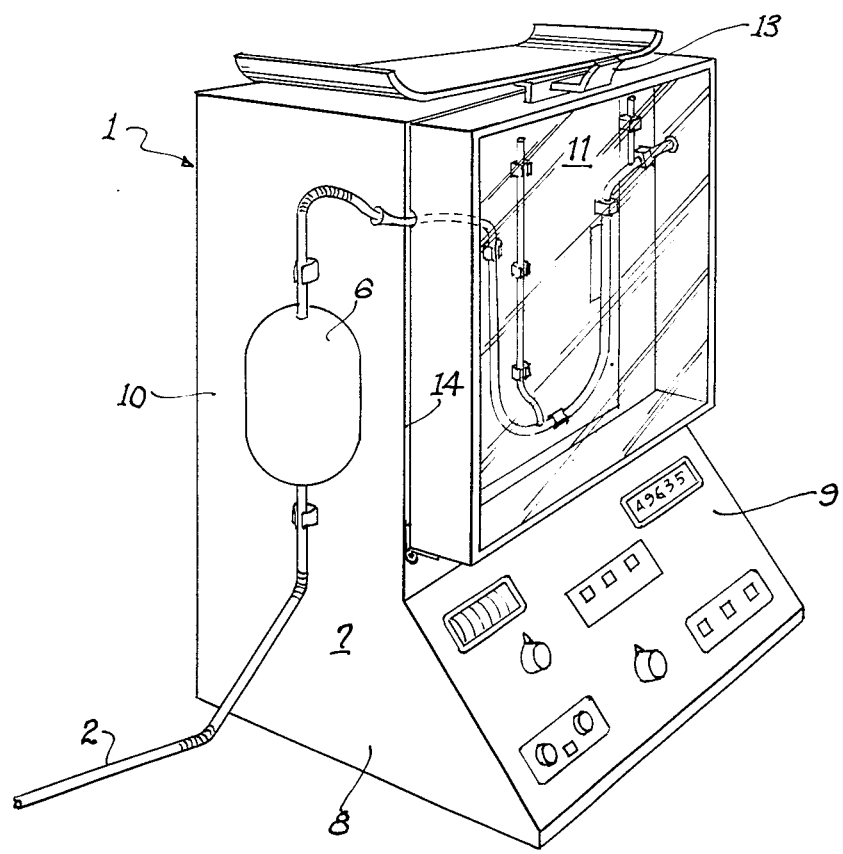
FIG. 2 is a perspective view of the preferred embodiment of the invention.

Referring now to the drawing and beginning with FIG. 1 which illustrates the general operation of the invention, the blood-loss accumulater 1 is shown mounted in series with a conduit 2 which leads from an intake nozzle 3 to a disposal tank 4. The intake nozzle 3 is intended to gather liquids from a surgical incision area by suction. The suction effect is provided by a pump 5 which draws air from the upper part of the sealed disposal tank 4. A filter 6 is placed on the conduit part of the blood-loss accumulator in order to capture small fragments of bones and other solids that might interfere with the operation of the accumulator.

The blood-loss accumulator 1 which is more specifically described in the remaining figures of the drawing comprises a cabinet 7 having a base 8 with a slanted front mounting a control panel 9. The upper part of the cabinet 10 has a glass front door 11 which pivots around a hinge 12 mounted horizontally along its base. A latching handle 13 holds the front door 11 against the front panel 14 of the instrument.

The front panel 14 forms a frame for a platen 15 which forms an integal part of a weighing apparatus.

Figure 3:
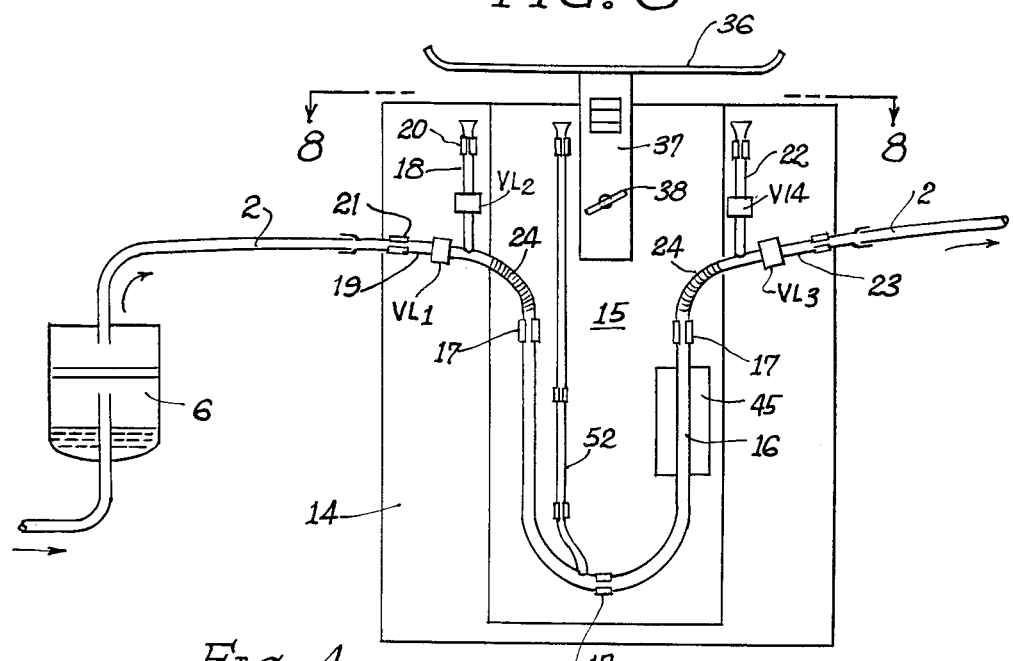
FIG. 3 is a diagrammatical view of the measurement section of the apparatus.

As more specifically illustrated in FIG. 3, a U-shaped tubular element 16 is attached to the platen 15 by three releasable clamps 17. The left end of the tubular element 16 branches out into an open-ended vertical section or vent 18 and a quasi-horizontal section 19 which attaches to the section of the conduit 2 coming from the filter 6. Both sections 18 and 19 are attached to the panel 14 by means of releasable clamps 20 and 21. Similar sections respectively numbered 22 and 23 are found on the right side of the U-shaped tubular section; with the quasi-horizontal element being connected to the section of the conduit 2 leading to the waste container. Flexible elbows 24 which span the separations between the platen 15 and the front panel 14 permit the platen to move up and down indefinitely out the front panel.

Four solenoid-controlled clamping valves VL1, VL2, VL3, Vl4 engage the respective vertical and horizontal sections 19, 18, 23 and 22. These valves are designed to pinch the walls of the tubing in order to interrupt the flow of liquid therethrough.

As shown in FIG. 9 each valve VL forms a cradle 25 which receives the tubing 26 shown in phantom line and a hammer 27 which is driven by the solenoid coil 28 into the cradle 25 thus pinching the tubing 26.

The weighing apparatus is more specifically illustrated in FIGS. 7 and 8. The platen 15 which supports the U-shaped tubular element 16 has its lateral edge slidingly engaged into two grooves of the front panel 14. The platen 15 is also suspended to a lever which pivots at 30 about bracket 31, applying a stretching force on the strain gage element 32 attached to the back panel 33 of the cabinet 7. A coil spring 34 attached to the roof 35 of the cabinet is used to balance the scale. A scale tray 36 supported by angle bracket 37 (not shown in FIG. 8) is detachably mounted on the face of the platen 15 by means of wing nut 38 the distortion imposed to the strain gage 32 by the weight of the components attached to the platen 15 is electronically interpreted into a digital weight indication in the electronic circuitry held on the printed circuit board 39.

Figure 5:
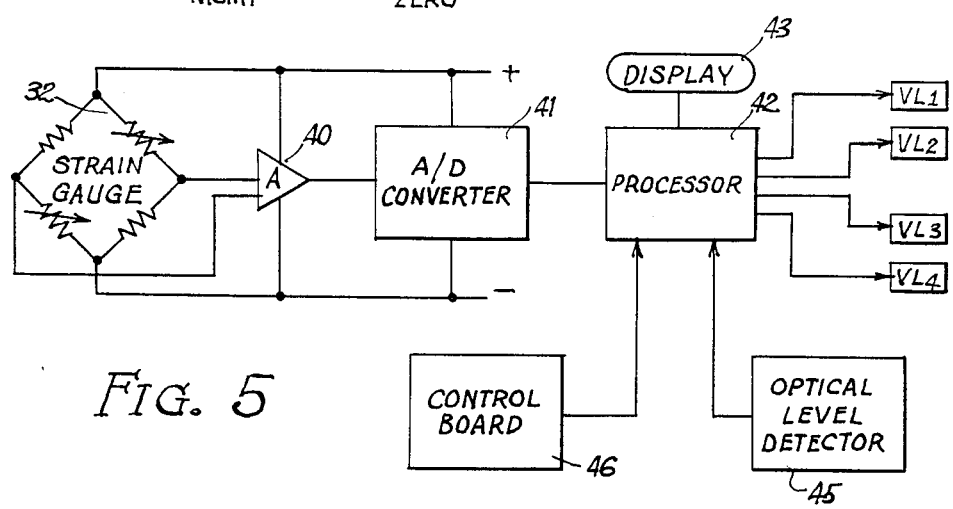
FIG. 5 is a block diagram of the apparatus control.

As illustrated in FIG. 5, the differentiated output signals from the strain gage 32 are processed through an amplifier 40. The analog output of the amplifier is then converted to a binary value by the analog to digital converter 41. The digital weight information is analyzed by a data processor 42 which, among other functions, causes the digital readout 43 to display the measured weight. It should be noted that the rearward position of the scale tray 36 reduces the amount of torque exerted on the strain gage 32 by any item placed on that tray. By comparison, the weight of the components attached to the face of the platen 15 can be weighted with greater sensitivity, due to the distance between them and the pivotal point 30 of lever 31.

Figure 4:
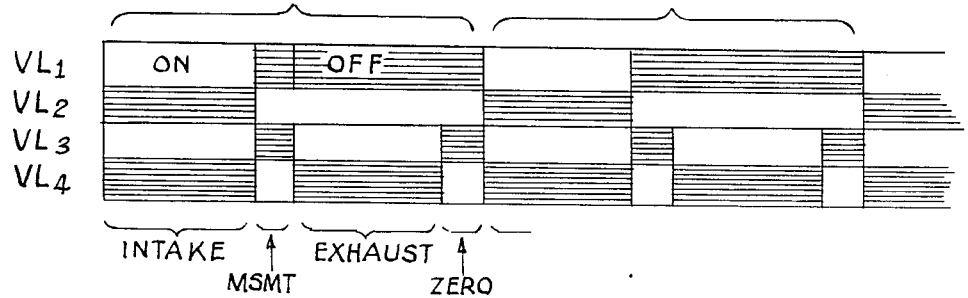
FIG. 4 is a timing diagram of the flow-controlling valves.

The processor is programmed to sequentially control the operation of the solenoid-controlled valves VL1–VL4 according to the timing diagram illustrated in FIG. 4. During the flow of fluid in the conduit 2, the action of the valves causes successive samplings of the fluid to be momentarily trapped in the U-shaped part of the tube 16 where they can be measured in terms of weight and volume.

The volume of liquid momentarily held in the U-shaped tubular element 16 is measured by means of an optical level detector 45. Which is applied against the right arm of the tube. The optical level detector 45 comprises a series of light emitters 47 and light sensors 48. As shown in FIG. 10 each light emitter 47 is shaped and located to direct a collimated beam of light 49 into the fluid-carrying tube 16. The associated light sensor 48 is located to receive the beam 50 reflected by the internal wall of the tube 16. The presence of fluid in the tube 16 causes a premature partial reflection and a refraction of beam 49 which defuses it and reduces the amount of light received by the sensor 48.

The optical level detector 45 is first used to detect the fact that the sufficient liquid is present in the tube 16 to constitute a valid sampling and to trigger the measurement sequence. Secondly, the various pairs of sensors 47 and 48 are used to determine the exact level of the liquid in the tube during the volumetric measurement sequence. The outputs from the optical level detector 45 are fed to the processor 42 to be interpreted into an actual volumetric value and in combination with the weight of the sampling into a density measurement.

The knobs and switches which appear on the control panel 9 are directly connected to a printed circuit board board 46 which is also tied to the main electronic printed circuit board 39 which holds the processor 42.

It should be noted that when the front door 11 of the cabinet 7 is open a toe 51 at the base of the door 11 pushes the scale platen 15 into a locked position. This allows for the clipping and removal of the U-shaped tubular element 16 without disturbing or damaging the sensitivity of the scale.

The operation of the instrument can be best understood by reference to FIGS. 4, 5 and 6.

The normal model operation of the apparatus can be divided in repetitive cycles of four stages each. The first stage corresponds to the intake of fluid into the U-shaped tube section 16. With valves VL1 and VL3 open and VL2 and VL4 closed, fluid is drawn from the nozzle 3 through the filter 6 and into section 16. When the level of fluid in section 16 reaches the area of the optical level detector 45 valves VL1 and VL3 are closed and VL2 and VL4 are opened. This begins the second stage during which the volume and weight of the liquid trapped in section 16 are measured. The opening of valves VL2 and VL4 allow the sampling of fluid trapped in section 16 to settle evenly in the U-shaped section under atmospheric pressure. With some viscous liquid or when using small diameter tubing it might be necessary to provide a small diameter chimney 52 in order to evacuate any air bubble which may be trapped in the bottom part of the U-shaped section. At this time the force exerted on the strain gage 32 by the fluid loaded platen 15 is read by the processor 42. Next, the processor scans the light sensors 48 in order to determine the level reached by the fluid in section 16.

At the end of a predetermined period of time the third stage is initiated by opening valve VL3 and closing VL4. At that point the fluid is sucked out of section 16 and into the disposal tank 4 under the action of the pump 5.

At the end of a second predetermined time the fourth stage is started by closing valve VL3 and opening valve VL4 during that last stage the weight of the platen is read by the processor and this measurement is subtracted from the value read during the second stage in order to obtain the precise weight of the liquid sampling alone.

After a third predetermined time a new cycle is initiated by opening valves VL1 and VL3 and closing valves VL2 and VL4.

The weights and volumes of the samplings thus obtained can be used to determine the exact amount of blood passing through the apparatus when as in this case the fluid is constituted by a mixture of patient's blood and irrigating solution.

For instance, given the patient's blood density DSB and knowing the solution density DSS, the volume of blood VOB contained in a sampling whose weight WGX and volume VOX have been measured can be obtained from the following equation:

$$VOB = VOX \times \frac{\frac{WGX}{VOX} - DSS}{DSB - DSS}$$

These calculations are performed by the processor 42. The known density of the patient's blood can be dialed on a set of thumb-wheel switches 52 mounted on the control panel 9. Alternately, and when possible, a small sample of the patient's blood could be drawn into the apparatus which will then automatically measure its density and store it for future use. The same applies to the irrigation solution whose density can either be dialed in or measured by running a sample of pure solution through the apparatus.

The processor is programmed to accumulate the repetitive blood volume measurements and to display the results on a numerical readout 53 located on the control panel 9.

The various modes of operation will now be explained with reference to the control panel 9 illustrated in FIG. 6.

Before starting normal operation, the apparatus must be calibrated. With the FUNCTION switch set to CALIBRATION, the TYPE switch is set to SOLUTION. If the density of the irrigating solution is already known it can be dialed on the thumb-wheel switches 52, and then entered by placing the MODE switch to DIAL and pressing the SET push button. The density value dialed on the switches 52 will be automatically entered into the system as DSS. If this value is not known, the MODE switch must be set to AUTO, and a sample of pure irrigating solution must be drawn into the apparatus throught the conduit 2. Upon pressing the SET push button a sampling of the solution will be weighted and volumetrically measured. The instrument will compute the corresponding density DSS and store it for future use.

The same calibrating operation must be done in connection with the patient's blood by placing the TYPE switch to BLOOD.

Once the instrument has been calibrated normal operation may begin. The FUNCTION switch must be set to ACCUMULATION. Pressing the RESET push button will clear the accumulator and the readout 53 will display 0 cubic centimeters. As soon as the blood-and-irrigation solution mixture begins to flow through the system, the RUN push button must be pressed in order to initiate the accumulation process. If the apparatus has not been previously calibrated, i.e. if the blood density DSB and the solution density DSS have not been entered, the accumulation will be aborted and a NOT CALIBRATED warning will appear in the error message area 54 of the control panel.

The accumulation can be stopped at any time by pressing the HOLD push button, without resetting the current accumulation shown in the readout 53. The accumulation can be restarted by pressing the RUN push button.

The instrument can also be used as a scale for weighing sponges and linen which have been saturated with the blood and solution mixture.

The scale tray 36 must first be installed by attaching the leg of the bracket 37 to the face of the platen 15 by means of wing screw 38. Next, the scale can be tared by turning the FUNCTION switch to the SCALE position. The DRY WEIGHT switch shold be set to the OFF position. Pressing the TARE push button will cause the scale to calibrate itself automatically. The readout 53 will display the weight of 0 grams regardless of the weight of any components attached to the platen or that of any object placed on the scale tray 36. At this point objects to be weighed can be placed on the tray 36 and their weight can be obtained by pressing the WEIGH push button. The corresponding weight will automatically appear on the readout 53.

In the case where mixture-saturated items must be weighed and the corresponding volume of blood must be added to the accumulation the following procedure must be followed.

First, it is necessary to enter the dry weight of these items into the apparatus. If this weight is already known it can be dialed directly on the thumbwheel switches 52 and entered by placing the DRY WEIGHT switch to manual and pressing the WEIGH push button. Alternately, the actual items may be weighed by first taring the scale as previously described, then placing the DRY WEIGHT switch to auto and placing the dry items on the scale tray 36. Pressing the WEIGH push button while the DRY WEIGHT switch in the AUTO position, will cause the actual weight of the dry items to be stored for future use.

At the end of the surgical operation, these items can be gathered and weighed again in order to determine the amount of blood which has been absorbed. For this measurement, the scale should be first tared with the tray 36 empty. The items may then be loaded on the tray and weighed by pressing the WEIGH push button. After which the corresponding amount of blood which has been absorbed by the weighed items can be automatically added to the accumulation by pressing the ADD push button. The instrument will automatically subtract from the measured weight the dry weight of the items which had been previously entered, then compute the actual corresponding volume of blood absorbed by the items, using the blood and solution density entered during the calibration sequence, and the last mixture density measured by the instrument.

Any attempt to use the scale without first going through the taring sequence will cause the message SCALE NOT TARED to be flashed on the error message area 54 of the control panel. Similarly, if one attempts to add the corresponding volume of blood held by the saturated items, without first having entered their dry weight, the message NO DRY WEIGHT will appear on the error message area 54.

The operation of the instrument which has just been described is done under control of the processor 42 which is installed on the printed circuit board 39. The processor and associated circuitry, the optical level detector 45, the strain gage 32 and the circuitry of the control board 46 are powered from a battery 55 housed within the cabinet 7.

The operation of the processor 42 is controlled by a sequence of standard instructions which may vary according to the type of hardware used, and are well known to those skilled in the programming art; in connection with some programming routines which are given below in high level language with mnemonics explanations.

PROGRAM

-continued

| | |
|---|---|
| 10 | IF RUN= I GO TO 40 |
| 20 | IF RST= I LET CMV= ZIN= BCA= SCA= COK= 0 |
| 30 | IF SCL= I GO TO 610 |
| 40 | LET VL2= VL4= 0 |
| 50 | LET VL1= VL3= I |
| 60 | READ VOX |
| | IF VOX <ILV GO TO 60 |
| 100 | LET VL1= VL3= TIM= 0 |
| 110 | LET VL2= VL4= I |
| 120 | READ TIM |
| 130 | IF TIM<MST GO TO 120 |
| 140 | READ WGX |
| 150 | READ VOX |
| 200 | LET VL4= 0 |
| 210 | LET VL3= I |
| 220 | LET DSX (WGX-ZER)/VOX |
| 230 | IF CAL= I, GO TO 500 |
| 240 | LET DSM= DSX |
| 250 | LET DEX= DSM-DSS |
| 260 | LET BPC= DEX/FSP |
| 270 | LET VOB= BPC X VOX |
| 280 | IF ADD=1 GO TO 320 |
| 310 | IF ZIN= 0 GO TO 350 |
| 320 | LET CMV= CMV + VOB |
| 350 | READ TIM |
| 360 | IF TIM <EXT GO TO 350 |
| 400 | LET VL3= 0 |
| 410 | LET VL4= I |
| 420 | READ TIM |
| 430 | IF TIM <ZET GO TO 420 |
| 440 | READ WGX |
| 450 | LET ZER= WGX |
| 460 | LET DIS= CMV |
| 470 | LET ZIN 1 |
| 480 | GO TO 20 |
| 500 | IF ACC=I LET ERI= I |
| 510 | IF ERI = I GO TO 1000 |
| 520 | IF DIC= I GO TO 560 |
| 530 | IF CAB= I LET DSB= DSX and BCA= I |
| 540 | IF CAB= 0 LET DSS= DSX and SCA = I |
| 550 | GO TO 580 |
| 560 | IF CAB=I LET DSB= DIA and BCA = I |
| 570 | IF CAB= 0 LET DSS= DIA and SCA = I |
| 580 | IF BCA= SCA= I LET FSP= DSB-DSS and COK= I |
| 590 | GO TO 10 |
| 610 | IF WGH= I GO TO 640 |
| 620 | IF TAR= I GO TO 640 |
| 630 | IF ADD= I GO TO 900 |
| 640 | READ WGX |
| 650 | IF WGH= I AND TST= 0 LET ER2= I |
| 660 | IF ER2= I GO TO 1000 |
| 670 | LET SCW= WGX - TAW |
| 680 | LET DIS= SCW |
| 690 | GO TO 610 |
| 700 | IF MAD= I GO TO 800 |
| 710 | READ WGX |
| 720 | IF WGH= I and TST= 0 LET ER2= I |
| 730 | IF ER2= I GO TO 1000 |
| 740 | LET DRW= WGX - TAW |
| 750 | LET DIS= DRW |
| 760 | LET DWS= I |
| 800 | READ DIA |
| 810 | LET DRW= DIA |
| 820 | LET DWS= I |
| 900 | IF COK= 0 LET ER1= I |
| 910 | IF ERI= I GO TO 1000 |
| 920 | IF DWS= 0 LET ER3= I |
| 930 | IF ER3= Z GO TO 1000 |
| 940 | LET WGX= SCW - DRW |
| 950 | LET VOX= WEX/DSX |
| 960 | GO TO 270 |
| 1,000 | ABORT |

MNEMONICS

| | |
|---|---|
| ACC | Accumulation Mode |
| ADD | Addition |
| BCA | Blood Calibration Set |
| BPC | Blood Percentage |
| CAB | Blood Calibration Mode |
| CAL | Calibration Mode |
| CMV | Commulative Volume |
| COK | Calibration OK |
| DEX | Excess Density |
| DIA | Dial |
| DIC | Dial Calibration |
| DIS | Display |
| DRW | Dry Weight |
| DSB | Blood Density |
| DSM | Mixture Density |
| DSS | Solution Density |
| DSX | Sample Density |
| DWS | Dry Weight Set |
| FRI-ER3 | Error |
| EXT | Exhaust time |
| FSP | Fullscale percentage |
| ILV | Intake Level |
| MAD | Manual dry weight |
| MST | Measurement settling time |
| RST | Reset |
| RUN | Run |
| SCA | Solution Calibration Set |
| SCC | Scale Mode |
| SCW | Scale Weight |
| TAR | Scale Tare Mode |
| TAW | Tare Weight |
| TIM | Time |
| TST | Tare Set |
| VL1-VL4 | Valves |
| VOB | Volume of Blood |
| VOX | Sample Volume |
| WGH | Weigh Mode |
| WGX | Sample Weight |
| SER | Empty Scale Weight |
| ZET | Zeroing Time |
| ZIN | Zeroing Done |

In the above listing the tens-series of instructions controls the intake of liquid into the U-shaped section 16 of the apparatus.

The hundreds series controls the measurement of weight and volume.

The two hundreds series of instructions controls the computation of blood volume.

The three hundreds series of instructions controls the accumulation of sampling volumes.

The four hundreds series of instructions controls the automatic zeroing of the scale.

The five hundreds series of instructions controls the calibration of the blood and irrigation solution densities.

The six hundreds series of instructions controls the operation of the scale.

The seven hundreds series of instructions controls the dry weight operation.

The eight hundreds series of instructions controls the dialing of dry weight.

The nine hundreds series of instructions controls the addition of the volume of blood absorbed by sponges, linen etc. to the displayed accumulation.

The accuracy of the bloodloss accumulation will depend greatly upon the difference of densities between the blood and the irrigation solution. The blood density is typically 1.02. It is possible to lower the density of the irrigation solution by adding ethanol, peroxide or certain salts, and obtain a density lower than 0.9.

Accuracy can be improved by increasing the size of the samplings. The U-shaped section 16 could be replaced by a pouch for that purpose. Whatever is used as the sampling area must be easily detachable from the apparatus so that it may be discarded after the surgical operation with the rest of the conduit 2.

As the size of the samplings is increased, the exhaust time could be maintained to a reasonable level by increasing the cross-diameter of the conduit 2. A long exhaust time which would interrupt the suction of blood-and-solution mixture through the system would be unacceptable. While the preferred embodiment of the invention has been described and modifications have been suggested, it should be understood that other embodiments could be devised based on the same principle of operation, which would remain within the spirit of the invention and the scope of the appended claims.

What is claimed is:

1. An apparatus for continuously accumulating the volume of a first fluid having a known density and being part of a mixture flowing intermittently through a conduit, the remaining part of the mixture being substantially comprised of a variable quantity of a second fluid having a known but different density than the density of the first fluid, which comprises:
   means for drawing the mixture of the first and second fluids through said conduit;
   means for measuring the volume of repetitive samplings of the mixture intermittently held within a predetermined section of the conduit;
   means for measuring the weight of said samplings;
   means, responsive to both of said means for measuring, for calculating the corresponding volume of the first fluid in each said sampling from the respective known densities of the first and second fluids in said mixture.

2. The apparatus claimed in claim 1 which further comprises:
   means for intermittently interrupting the circulation of the mixture through said section, and for trapping said samplings therein during said various measurings.

3. The apparatus claimed in claim 2 wherein said means for interrupting comprises clamping valves shaped and dimensioned to close the beginning and end of said predetermined section of the conduit.

4. The apparatus claimed in claim 3 wherein said means for measuring the volume comprise a fluid-level detector.

5. The apparatus claimed in claim 4 wherein said fluid level detector comprises a plurality of optical sensors located along a portion of said section.

6. The apparatus claimed in claim 3 wherein said means for measuring the weight comprise a scale having a panel supporting said section of conduit.

7. The apparatus claimed in claim 3 wherein said means for calculating comprises:
   means for determining the density of the mixture in each sampling;
   means for comparing said density to the respective densities of the first and second fluids;
   means for computing the volume of first fluid as a function of said densities and the weight of each said sampling.

8. The apparatus claimed in claim 2 which further comprises manual means for entering the known densities of said first and second fluids into said means for calculating.

9. The apparatus claimed in claim 3 which further comprises automatic means for varifying the density of each fluid in the absence of the other.

10. The apparatus claimed in claim 7 wherein said predetermined section of the conduit comprises a U-shaped tubular element having closable venting means.

11. The apparatus claimed in claim 7 wherein said means for measuring both the volume and the weight of each said samplings, means for calculating, means for determining, means for comparing and means for computing comprise:
    a programmable processor; and
    manual means for controlling the operation of said processor.

12. The apparatus claimed in claim 11 which further comprises:
    a scale; and
    means responsive to said scale for determining the volume of the first fluid corresponding to the weight derived from said scale.

* * * * *